(12) United States Patent
Kimura et al.

(10) Patent No.: US 11,992,177 B2
(45) Date of Patent: May 28, 2024

(54) IMAGE PROCESSING DEVICE FOR ENDOSCOPE, IMAGE PROCESSING METHOD FOR ENDOSCOPE, AND RECORDING MEDIUM

(71) Applicant: OLYMPUS CORPORATION, Tokyo (JP)

(72) Inventors: Mitsutaka Kimura, Hino (JP); Yamato Kanda, Hino (JP); Makoto Kitamura, Hachioji (JP); Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 350 days.

(21) Appl. No.: 17/238,865

(22) Filed: Apr. 23, 2021

(65) Prior Publication Data
US 2021/0251470 A1 Aug. 19, 2021

Related U.S. Application Data

(63) Continuation of application No. PCT/JP2018/039829, filed on Oct. 26, 2018.

(51) Int. Cl.
*A61B 1/00* (2006.01)
*A61B 1/045* (2006.01)
(Continued)

(52) U.S. Cl.
CPC ........ *A61B 1/000094* (2022.02); *A61B 1/045* (2013.01); *A61B 1/05* (2013.01); *G06T 7/0012* (2013.01)

(58) Field of Classification Search
CPC .......... A61B 1/00009; A61B 1/000094; A61B 1/00045; A61B 1/00055; A61B 1/00059;
(Continued)

(56) References Cited

U.S. PATENT DOCUMENTS

2006/0293558 A1* 12/2006 De Groen ............. G06T 7/0012
600/101
2008/0108873 A1* 5/2008 Gattani .................. A61B 1/045
382/128
(Continued)

FOREIGN PATENT DOCUMENTS

EP 1842481 A1 10/2007
EP 2692280 A1 2/2014
(Continued)

OTHER PUBLICATIONS

International Search Report dated Jan. 8, 2019 issued in PCT/JP2018/039829.

*Primary Examiner* — Timothy J Neal
(74) *Attorney, Agent, or Firm* — Scully, Scott, Murphy & Presser, P.C.

(57) ABSTRACT

An image processing device for an endoscope includes a processor. The processor receives, as input, a generated image acquired by performing predetermined processing on an image pickup signal acquired by an endoscope, analyzes a withdrawing speed of the endoscope based on at least one of the generated image and information relating to an operation state of the endoscope, detects a lesion part from the generated image, performs a diagnosis support action on the lesion part, decides a factor affecting the diagnosis support action based on an analysis result of the withdrawing speed, and outputs the factor.

24 Claims, 10 Drawing Sheets

(51) Int. Cl.
*A61B 1/05* (2006.01)
*G06T 7/00* (2017.01)

(58) Field of Classification Search
CPC .......... A61B 1/045; G06T 2207/10068; G06T 2207/30096
See application file for complete search history.

(56) References Cited

U.S. PATENT DOCUMENTS

| | | | |
|---|---|---|---|
| 2008/0292154 A1 | 11/2008 | Nishimura et al. | |
| 2010/0157037 A1 | 6/2010 | Iketani et al. | |
| 2011/0254937 A1* | 10/2011 | Yoshino | A61B 1/0655 348/E7.085 |
| 2011/0275889 A1* | 11/2011 | Kase | A61B 1/0005 600/103 |
| 2013/0278739 A1 | 10/2013 | Tanaka et al. | |
| 2014/0184769 A1 | 7/2014 | Ishihara et al. | |
| 2015/0238126 A1* | 8/2015 | Saito | A61B 1/000094 600/339 |
| 2017/0039707 A1* | 2/2017 | Akimoto | A61B 1/00045 |
| 2017/0086659 A1* | 3/2017 | Uchiyama | A61B 1/043 |
| 2017/0251932 A1* | 9/2017 | Kaku | A61B 5/02007 |
| 2018/0092515 A1 | 4/2018 | Yashiro et al. | |

FOREIGN PATENT DOCUMENTS

| | | |
|---|---|---|
| EP | 2912991 A1 | 9/2015 |
| EP | 3305169 A1 | 4/2018 |
| JP | 2003-265410 A | 9/2003 |
| JP | 2005-124756 A | 5/2005 |
| JP | 2006-166990 A | 6/2006 |
| JP | 2007-244518 A | 9/2007 |
| JP | 2010-142597 A | 7/2010 |
| JP | 2011-224038 A | 11/2011 |
| JP | 2011-255006 A | 12/2011 |
| JP | 2013-56001 A | 3/2013 |
| JP | 2015-177961 A | 10/2015 |
| JP | 2017-6489 A | 1/2017 |
| JP | 2017-86549 A | 5/2017 |
| JP | 2018-57605 A | 4/2018 |
| JP | 2018-139848 A | 9/2018 |
| WO | 2006/062163 A1 | 6/2006 |
| WO | 2013/035738 A1 | 3/2013 |
| WO | 2013/073418 A1 | 5/2013 |

* cited by examiner

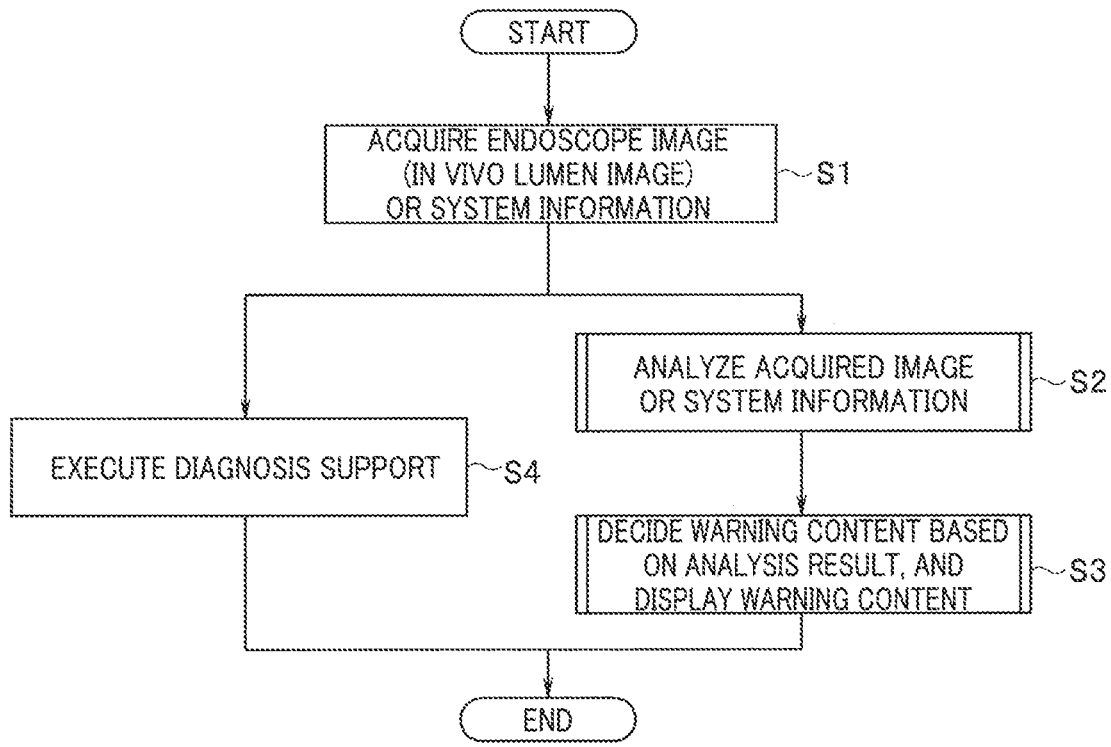
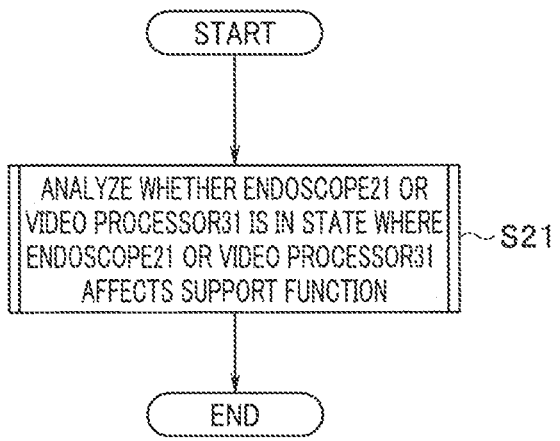

IMAGE PROCESSING DEVICE FOR ENDOSCOPE, IMAGE PROCESSING METHOD FOR ENDOSCOPE, AND RECORDING MEDIUM

CROSS REFERENCE TO RELATED APPLICATION

This application is a continuation application of PCT/JP2018/039829 filed on Oct. 26, 2018, the entire contents of which are incorporated herein by this reference.

BACKGROUND OF THE INVENTION

1. Field of the Invention

The present invention relates to an image processing device for an endoscope, an image processing method for an endoscope, and a recording medium.

2. Description of the Related Art

Conventionally, endoscopes have been widely used in a medical field and an industrial field. For example, in the medical field, an operator observes an endoscope image of an inside of a subject displayed on a display device to find and differentiate a lesion part, and can perform processing using a treatment instrument on the lesion part.

In general, an image processing device having a diagnosis support function is widely known, the diagnosis support function performing a highlighting display with a marker, such as a frame, such that the highlighting display is displayed on the lesion part detected from an endoscope image for the purpose of preventing an operator from overlooking the lesion part when the operator observes the endoscope image.

The diagnosis support function is a function effective at preventing overlooking a lesion part. However, when a highlighting display, such as detection frame display, is performed on a lesion part which the user is already aware of, such highlighting display may obstruct the user's observation.

In view of the above, Japanese Patent Application Laid-Open Publication No. 2011-255006, for example, proposes an endoscope image processing device where a highlighting display, such as a detection frame, is not performed even in the case where a lesion candidate is detected, when there is a high possibility that the user is already aware of the lesion candidate due to a large size of the lesion part.

SUMMARY OF THE INVENTION

One aspect of the present invention is directed to an image processing device for an endoscope including a processor, wherein the processor is configured to receive, as input, a generated image generated by performing predetermined processing on an image pickup signal acquired by picking up an image of an object by an endoscope, analyze a withdrawing speed of the endoscope based on at least one of the generated image and information relating to an operation state of the endoscope, detect a lesion part that is an observation target of the endoscope, from the generated image, and perform a diagnosis support action of adding support information to the lesion part, or of giving notification, and decide a factor affecting the diagnosis support action based on an analysis result of the withdrawing speed of the endoscope, and output the factor.

One aspect of the present invention is directed to an image processing method for an endoscope, the method including: receiving, as input, a generated image generated by performing predetermined processing on an image pickup signal acquired by picking up an image of an object by an endoscope; analyzing a withdrawing speed of the endoscope based on at least one of the generated image and information relating to an operation state of the endoscope; detecting a lesion part that is an observation target of the endoscope, from the generated image, and performing a diagnosis support action of adding support information to the lesion part, or of giving notification; and deciding a factor affecting the diagnosis support action based on an analysis result of the withdrawing speed of the endoscope, and outputting the factor.

One aspect of the present invention is directed to a recording medium that is a non-transitory recording medium which records a computer program, and is readable by a computer, wherein the computer program causes the computer to acquire a generated image generated by performing predetermined processing on an image pickup signal acquired by picking up an image of an object by an endoscope, analyze a withdrawing speed of the endoscope based on at least one of the generated image and information relating to an operation state of the endoscope, detect a lesion part that is an observation target of the endoscope, from the generated image, and perform a diagnosis support action of adding support information to the lesion part, or of giving notification, and decide a factor affecting the diagnosis support action based on an analysis result of the withdrawing speed of the endoscope, and output the factor.

BRIEF DESCRIPTION OF THE DRAWINGS

FIG. 4 is a flowchart for describing one example of the flow of action confirmation processing relating to a diagnosis support function performed by the image processing device according to the first embodiment;

FIG. 5 is a flowchart for describing one example of the flow of acquired information analysis processing according to the first embodiment;

DETAILED DESCRIPTION OF THE PREFERRED EMBODIMENTS

Hereinafter, embodiments of the present invention will be described with reference to drawings.

First Embodiment

Figure 1:
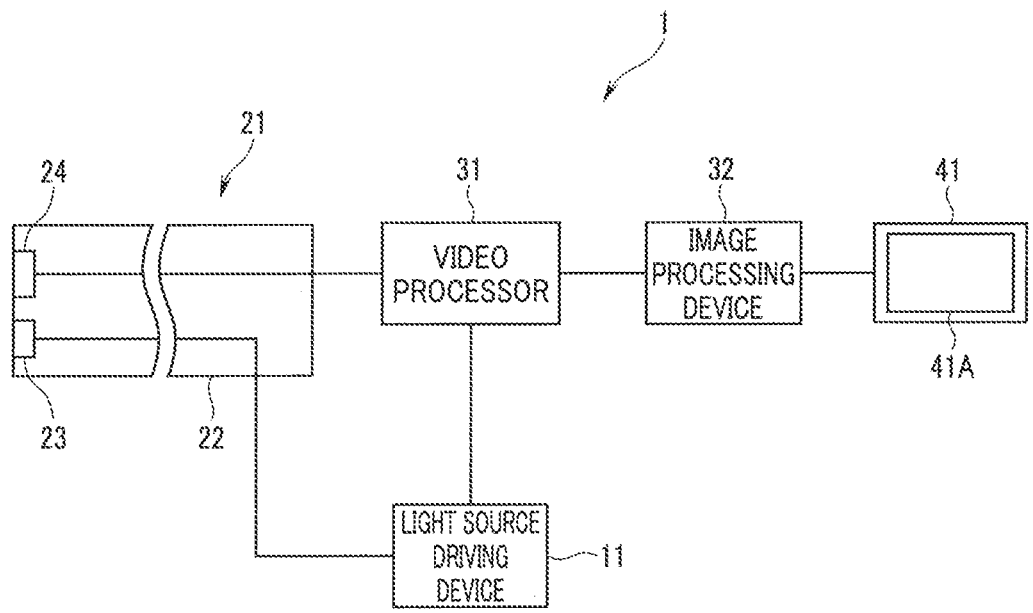
FIG. 1 is a view showing a configuration of a main part of an endoscope system including an image processing device according to an embodiment of the present invention.

FIG. 1 is a view showing a configuration of a main part of an endoscope system including an image processing device according to a first embodiment. As shown in FIG. 1, an endoscope system 1 is configured to include a light source driving device 11, an endoscope 21, a video processor 31, an image processing device for an endoscope (hereinafter referred to as "image processing device") 32, and a display device 41.

The light source driving device 11 is configured to include a drive circuit, for example. The light source driving device 11 is connected to the endoscope 21 and the video processor 31. The light source driving device 11 is configured to generate a light source drive signal for driving a light source unit 23 of the endoscope 21 based on a light source control signal outputted from the video processor 31, and to output the generated light source drive signal to the endoscope 21.

The endoscope 21 is connected to the light source driving device 11 and the video processor 31. The endoscope 21 is configured to include an elongated insertion portion 22 which can be inserted into the body cavity of a subject. The light source unit 23 and an image pickup unit 24 are provided to the distal end portion of the insertion portion 22.

The light source unit 23 is configured to include a light emitting element, such as a white LED. The light source unit 23 is configured to emit light corresponding to the light source drive signal, outputted from the light source driving device 11, to generate illumination light, and ejects the generated illumination light to an object, such as living tissue.

The image pickup unit 24 is configured to include an image sensor, such as a color CCD or a color CMOS. The image pickup unit 24 is configured to perform an action corresponding to an image pickup control signal outputted from the video processor 31. The image pickup unit 24 is configured to receive reflected light from the object illuminated by the illumination light from the light source unit 23, to pick up an image of the received reflected light to generate an image pickup signal, and outputs the generated image pickup signal to the video processor 31.

The video processor 31 is connected to the light source driving device 11 and the endoscope 21. The video processor 31 is configured to generate the light source control signal for controlling a light emission state of the light source unit 23, and to output the light source control signal to the light source driving device 11. The video processor 31 is configured to generate the image pickup control signal for controlling the image pickup action of the image pickup unit 24, and to output the image pickup control signal. The video processor 31 performs predetermined processing on the image pickup signal outputted from the endoscope 21 to generate a generated image of the object. The video processor 31 is configured to perform highlight processing or white balance correction processing, corresponding to user settings, on the generated image, which is generated and, thereafter, to sequentially output the generated image frame by frame to the image processing device 32.

Figure 2:
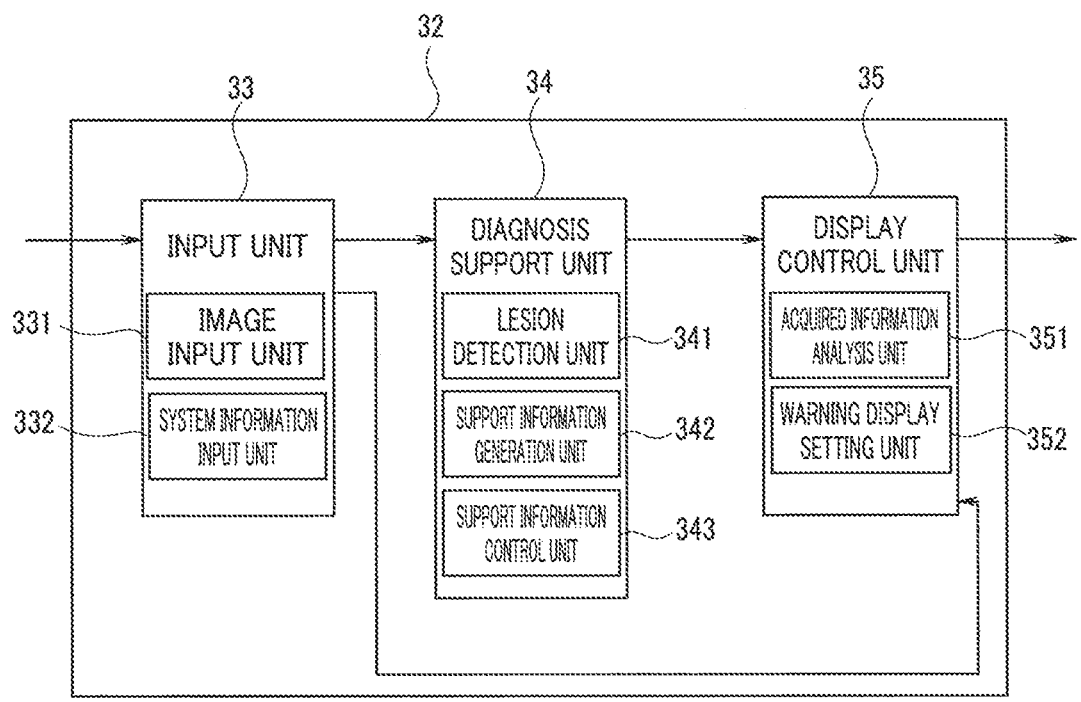
FIG. 2 is a block diagram for describing one example of a configuration relating to image processing performed by the image processing device according to a first embodiment.

The image processing device 32 includes a processor for image processing. The processor is configured to include an electronic circuit, such as an image processing circuit. However, the configuration is not limited to such a configuration. The processor may be configured such that software is executed by a CPU or the like in order to carry out functions of respective portions in the image processing device 32. Alternatively, the processor may be configured to include an integrated circuit, such as an FPGA (field programmable gate array), including a circuit unit which corresponds to the respective portions in the image processing device 32. The image processing device 32 is configured to generate a display image based on the generated image outputted from the video processor 31, and to perform an action causing the generated display image to be displayed on the display device 41. As shown in FIG. 2, the image processing device 32 is configured to include an input unit 33, a diagnosis support unit 34, and a display control unit 35. FIG. 2 is a block diagram for describing one example of a configuration relating to image processing performed by the image processing device according to the first embodiment.

The input unit 33 is configured to include an image input unit 331 and a system information input unit 332. The image input unit 331 outputs a generated image, which is inputted from the video processor 31, to the diagnosis support unit 34 and the display control unit 35. The system information input unit 332 acquires various types of information including version information or the like of the endoscope 21 and the video processor 31, and outputs the various types of information to the display control unit 35.

The diagnosis support unit 34 is configured to include a lesion detection unit 341, a support information generation unit 342, and a support information control unit 343.

The lesion detection unit 341 is configured to detect a lesion part contained in the generated image sequentially outputted from the image input unit 331. The lesion detection unit 341 performs processing of using an image discriminator for the generated image to detect a lesion part from the generated image. The image discriminator acquires in advance a function of being capable of discriminating a polyp image by a learning technique, such as deep learning. Note that a technique for detecting a lesion part is not limited to the above-mentioned learning technique, but another technique may be used. For example, a polyp candidate detection processing disclosed in Japanese Patent Application Laid-Open Publication No. 2007-244518 may be used.

To cause the user to recognize the presence of the lesion part detected by the lesion detection unit 341, the support information generation unit 342 performs a support information addition processing of generating a marker image surrounding the lesion part, and adding the marker image to the generated image, or displaying the marker image, for example. The marker image added by the support information generation unit 342 may have any mode provided that the marker image can present the presence of the lesion part as visual information. For example, the marker image may have any shape, such as a quadrangular shape, a triangular shape, a circular shape, or a star shape. Further, the marker image may be an image which does not surround a lesion part provided that the image can indicate the presence of the lesion part. For example, the presence of the lesion part may be indicated by causing the lesion part to have brightness or a color tone different from brightness or a color tone of a peripheral region. A configuration may also be adopted where a message indicating a lesion part is generated as support information, and is displayed in the vicinity of the lesion part in the form of a pop-up message or the like to indicate the presence of the lesion part.

The support information control unit 343 determines whether to generate support information for the lesion part detected by the lesion detection unit 341 and to add and display the support information, or controls display timing of the support information.

The display control unit 35 is configured to include an acquired information analysis unit 351 and a warning display setting unit 352.

Figure 3A:
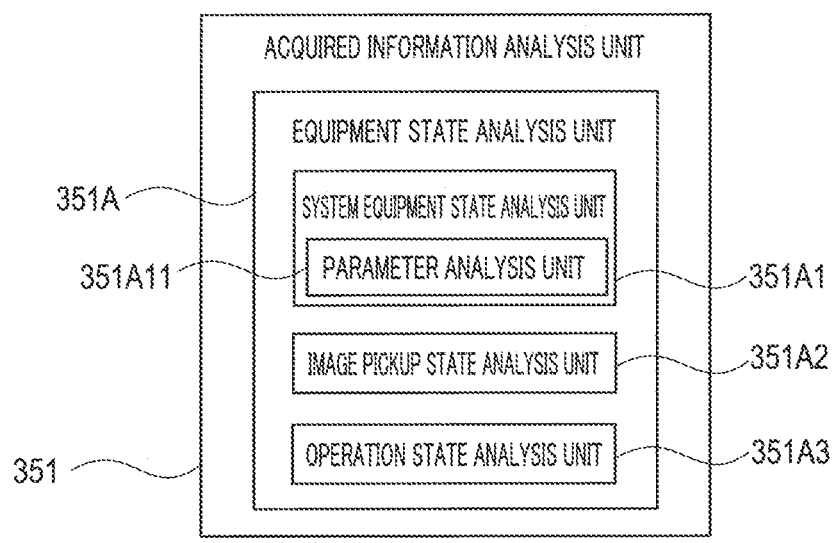
FIG. 3A is a block diagram showing a configuration of an acquired information analysis unit.

The acquired information analysis unit 351 is a circuit which analyzes generated images outputted from the input unit 33 and various types of information to determine whether the execution of a diagnosis support function of the diagnosis support unit 34 is affected. FIG. 3A is a block diagram showing the configuration of the acquired information analysis unit 351. Actions of the respective units of the acquired information analysis unit 351 shown in FIG. 3A will be described at corresponding portions in the description made hereinafter. FIG. 3A shows not only the configuration relating to the present embodiment which will be described below, but also the configurations relating to second to fourth embodiments which will be described after the present embodiment.

Figure 3B:
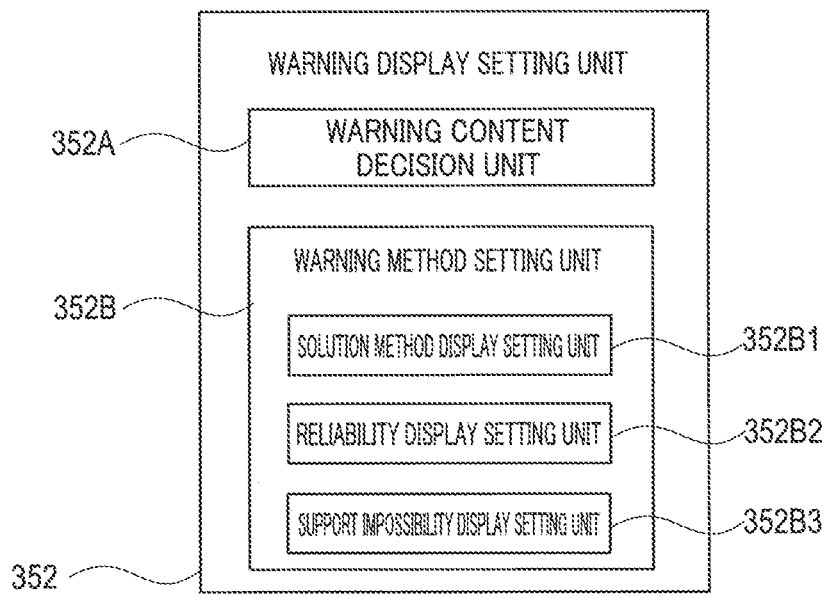
FIG. 3B is a block diagram showing a configuration of a warning display setting unit.

The warning display setting unit 352 is a circuit which identifies, based on the analysis result from the acquired information analysis unit 351, the cause for the diagnosis support not being correctly executed as the warning content, and which sets the display content causing the condition of the diagnosis support function including the warning to be displayed on a display screen 41A of the display device 41. FIG. 3B is a block diagram showing the configuration of the warning display setting unit 352. Actions of respective portions in the warning display setting unit 352 shown in FIG. 3B will be described at corresponding portions in the description made hereinafter. FIG. 3B shows not only the configuration relating to the present embodiment which will be described below, but also the configurations relating to second to fourth embodiments which will be described after the present embodiment.

The display device 41 is configured to include a monitor or the like to allow a display image outputted from the image processing device 32 to be displayed.

Next, the manner of operation in the present embodiment will be described. FIG. 4 is a flowchart for describing one example of the flow of action confirmation processing relating to the diagnosis support function performed by the image processing device according to the first embodiment.

For example, when power is supplied to the light source driving device 11 and the video processor 31, the endoscope 21 ejects illumination light to the object, receives reflected light from the object, picks up an image of the received reflected light to generate an image pickup signal, and then outputs the generated image pickup signal to the video processor 31.

The video processor 31 performs predetermined processing on the image pickup signal outputted from the endoscope 21 to generate a generated image of the object, and sequentially outputs the generated image, which is generated, to the image processing device 32 frame by frame. In other words, the image input unit 331 of the input unit 33 acquires an endoscope image (generated image) that is an in vivo lumen image, from the video processor 31 (S1). In the video processor 31 and the endoscope 21 (S1), the system information input unit 332 of the input unit 33 acquires system identification information stored in memories or the like not shown in the drawing. The image input unit 331 outputs the acquired image to the lesion detection unit 341 and the acquired information analysis unit 351. The system information input unit 332 also outputs the acquired system information to the acquired information analysis unit 351.

Note that it is sufficient for the acquired information analysis unit 351 to acquire at least either one of the generated image or the system information in S1. Needless to say, the acquired information analysis unit 351 may acquire both the generated image and the system information.

Next, the acquired information analysis unit 351 analyzes the generated image and/or the system information acquired in S1 (S2). The processing in S2 is executed by the procedure shown in FIG. 5, for example. FIG. 5 is a flowchart for describing one example of the flow of acquired information analysis processing according to the first embodiment. As shown in FIG. 5, in the acquired information analysis processing in the present embodiment, an analysis is made, based on the generated image and/or the system information, on whether the endoscope 21 or the video processor 31 is in a state where the endoscope 21 or the video processor 31 affects diagnosis support (S21). An equipment state analysis unit 351A shown in FIG. 3A relates to the processing in S21.

Figure 6:
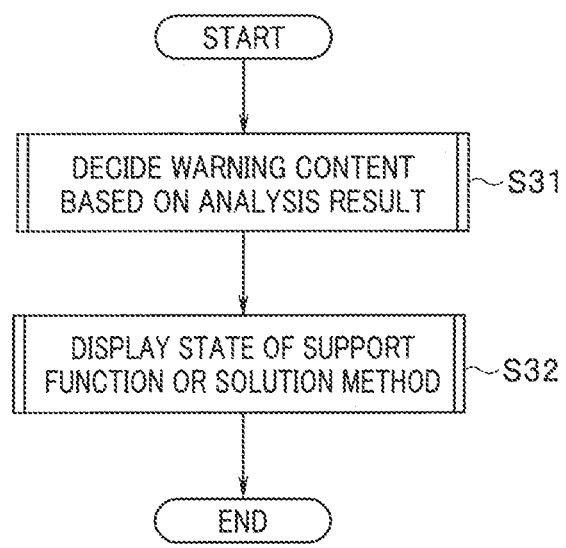
FIG. 6 is a flowchart for describing one example of the flow of display content generation processing based on the analysis result according to the first embodiment.

Return to the flow in FIG. 4. When it is determined, based on the analysis result acquired in S2, that the execution of the diagnosis support function is affected, the cause is identified as the warning content, and the display content is set so as to cause the condition of the diagnosis support function including the warning to be displayed on the display screen 41A of the display device 41 (S3). The processing in S3 is executed by the procedure shown in FIG. 6, for example. FIG. 6 is a flowchart for describing one example of the flow of display content generation processing based on the analysis result according to the first embodiment.

As shown in FIG. 6, in the display content generation processing based on the analysis result according to the present embodiment, first, a factor affecting the execution of the diagnosis support function is identified as the warning content based on the analysis result acquired in S2 (S31). A warning content decision unit 352A shown in FIG. 3B relates to the processing in S31. Next, the display content which is to be displayed on the display screen 41A of the display device 41 is set and outputted (S32). A warning method setting unit 352B shown in FIG. 3B relates to the processing in S32. It is preferable that the display content be a method for canceling the warning, or the state of the diagnosis support function, for example. However, in the case where the canceling method cannot be presented, the warning content per se decided in S31 may be displayed.

The diagnosis support function using the generated image inputted to the lesion detection unit 341 in S1 is executed in the diagnosis support unit 34 in parallel with the acquired information analysis processing in S2 (S4). Note that the processing in S4 can be executed in parallel with the processing in S2, but it is not always necessary to execute the processing in S4 in parallel with the processing in S2. It is also possible to sequentially execute the processing in the order of S2, S3, and S4. Alternatively, the processing in S4 may be executed before the processing in S2 is executed.

As described above, according to the above-mentioned embodiment, an analysis is made, by using the generated image and/or the system information of the endoscope 21 and the video processor 31, on whether the execution of the diagnosis support function is affected. When it is determined that the execution of the diagnosis support function is affected, the cause is identified, and is displayed on the display device 41 as warning. Accordingly, the user can always identify the action condition of the diagnosis support function.

Second Embodiment

In the above-mentioned first embodiment, the analysis is made, by using the generated image and/or the system information of the endoscope 21 and the video processor 31, on whether the execution of the diagnosis support function is affected. The present embodiment differs from the first embodiment in that an analysis is made from a plurality of viewpoints by using a generated image and/or system information of the endoscope 21 and the video processor 31, and the warning content is decided according to priority corresponding to the viewpoint.

An image processing device of the present embodiment has a configuration substantially the same as the configuration of the image processing device 32 of the first embodiment. The same components are given the same reference symbols, and the repeated description will be omitted.

The action confirmation processing relating to the diagnosis support function and performed by the image processing device of the present embodiment is substantially the same as the processing procedures shown in FIG. 4, FIG. 5, and FIG. 6, but differs in that an analysis is made from the plurality of viewpoints in the procedure (S21), shown in FIG. 5, for analyzing whether the endoscope 21 or the video processor 31 is in a state where the endoscope 21 or the video processor 31 affects the diagnosis support function. Further, the procedure (S31), shown in FIG. 6, for identifying a factor affecting the execution of the diagnosis support function as the warning content based on the analysis result differs in that the warning content is decided by using the analysis result from the plurality of viewpoints. Hereinafter, processing different from the processing in the first embodiment will be described.

Figure 7:
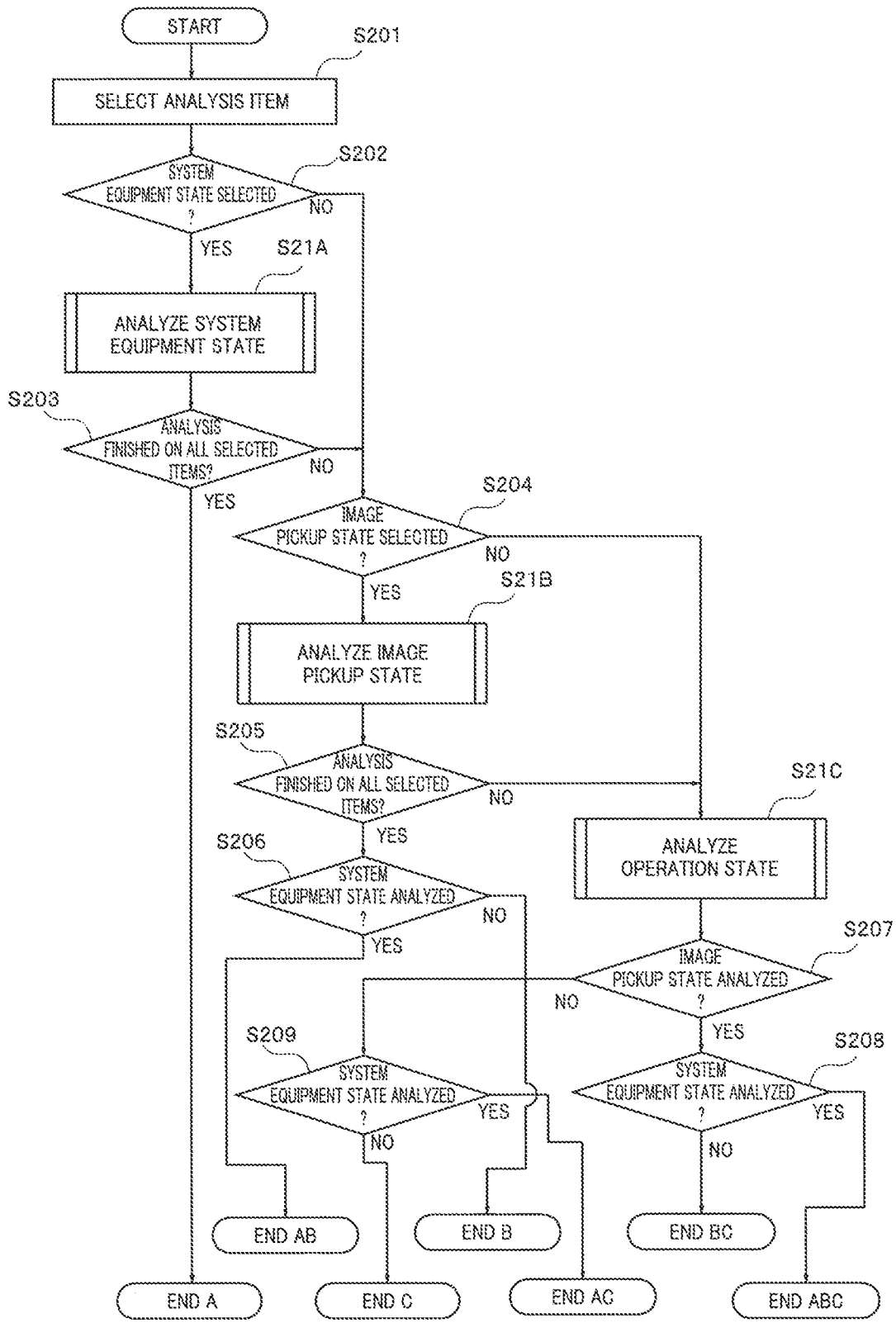
FIG. 7 is a flowchart for describing one example of the flow of function propriety analysis processing according to a second embodiment.

First, the procedure for analyzing whether the endoscope 21 or the video processor 31 is in a state where the endoscope 21 or the video processor 31 affects the diagnosis support function (FIG. 5, S21) will be described. The processing in S21 is executed by the procedure shown in FIG. 7, for example. FIG. 7 is a flowchart for describing one example of the flow of function propriety analysis processing according to a second embodiment. Respective analysis units (a system equipment state analysis unit 351A1, an image pickup state analysis unit 351A2, and an operation state analysis unit 351A3) included in the equipment state analysis unit 351A shown in FIG. 3A relate to the processing shown in FIG. 7. Note that in the present embodiment, the description will be made with respect to the case where an analysis is made, from the plurality of viewpoints, on whether the endoscope 21 or the video processor 31 is in the state where the endoscope 21 or the video processor 31 affects the diagnosis support function. However, FIG. 7 also shows a case where an analysis is made from only one viewpoint.

In analyzing whether the endoscope 21 or the video processor 31 is in the state where the endoscope 21 or the video processor 31 affects the diagnosis support function in S21, first, a plurality of items are selected from items (viewpoints) on which an analysis is made (S201). Examples of the viewpoints for the analysis may be items, such as (A) system equipment state, (B) image pickup state, and (C) operation state. In the present embodiment, two or more items are selected from these items to make the analysis.

When (A) system equipment state is selected as the analysis item (S202, YES), the processing advances to S21A to execute the analysis. The system equipment state analysis unit 351A1 relates to the analysis of the system equipment state which is executed in S21A. The system equipment state analysis unit 351A1 receives, as input, system information of each piece of equipment forming the endoscope system, such as the endoscope 21 or the video processor 31, the system information being inputted from the system information input unit 332. The system equipment state analysis unit 351A1 analyzes, based on the system information of each piece of equipment, whether each piece of system equipment is in a state appropriate for the diagnosis support function. When the analysis is executed on all selected items (S203, YES), the processing reaches end A, and a function state analysis processing is finished.

In contrast, when (A) system equipment state is not selected as the analysis item (S202, NO), the processing advances to S204. Also when the analysis is not executed on any of all selected items (S203, NO), the processing advances to S204. When (B) image pickup state is selected as the analysis item (S204, YES), the processing advances to S21B to execute the analysis. The image pickup state analysis unit 351A2 relates to the analysis of the image pickup state which is executed in S21B. Based on the generated image inputted from the image input unit 331, the image pickup state analysis unit 351A2 analyzes whether the image pickup state is appropriate for the diagnosis support function. When the analysis is not executed on any of all selected items (S205, NO), the processing advances to S21C. Also when the image pickup state is not selected in S204 (S204, NO), the processing advances to S21C.

In S205, when the analysis is executed on all selected items (S205, YES), the processing advances to S206. When the system equipment state is also analyzed (S206, YES), the processing reaches end AB, and the function state analysis processing is finished. When the system equipment state is not analyzed, but only the image pickup state is analyzed (S206, NO), the processing reaches end B, and the function state analysis processing is finished.

The analysis is executed on (C) operation state, which is a remaining item, in S21C. The operation state analysis unit 351A3 relates to the analysis of the operation state in S21C. Based on information relating to the system, which is inputted from the system information input unit 332, and the generated image, which is inputted from the image input unit 331, the operation state analysis unit 351A3 analyzes whether the operation state of the endoscope 21 operated by the user is appropriate for the diagnosis support function. Next, the processing advances to S207 to check whether the image pickup state is analyzed.

When the image pickup state is also analyzed (S207, YES), the processing advances to S208 to check the execution/non-execution of the analysis of the system equipment state. When the system equipment state is also analyzed (S208, YES), the processing reaches end ABC, and the function state analysis processing is finished. In contrast, when the system equipment state is not analyzed (S208, NO), the processing reaches end BC, and the function state analysis processing is finished.

In contrast, when the image pickup state is not analyzed (S207, NO), the processing advances to S209 to check the execution/non-execution of the analysis of the system equipment state. When the system equipment state is analyzed (S209, YES), the processing reaches end AC, and the function state analysis processing is finished. In contrast, when the system equipment state is not analyzed either (S209, NO), the processing reaches end C, and the function state analysis processing is finished.

In other words, when the analysis relating to the selected items is finished, all analysis results relating to the items on which the analysis is executed are outputted. For example, when two items of (A) system equipment state and (B) image pickup state are selected as the analysis items, S21A and S21B shown in FIG. 7 are executed. The processing reaches end AB, the analysis result acquired by executing S21A and the result acquired by executing S21B are outputted, and the function state analysis processing is finished. When two items of (B) image pickup state and (C) operation state, for example, are selected as the analysis items, S21B and S21C shown in FIG. 7 are executed. The processing reaches end BC, the analysis result acquired by executing S21B and the result acquired by executing S21C are outputted, and the function state analysis processing is finished.

When two items of (A) system equipment state and (C) operation state, for example, are selected as the analysis items, S21A and S21C shown in FIG. 7 are executed. The processing reaches end AC, the analysis result acquired by executing S21A and the result acquired by executing S21C are outputted, and the function state analysis processing is finished. When three items of (A) system equipment state, (B) image pickup state, and (C) operation state, for example, are selected as the analysis items, all of S21A, S21B, and S21C shown in FIG. 7 are executed. The processing reaches end ABC, the analysis result acquired by executing S21A, the result acquired by executing S21B, and the result acquired by executing S21C are outputted, and the function state analysis processing is finished.

Figure 8:
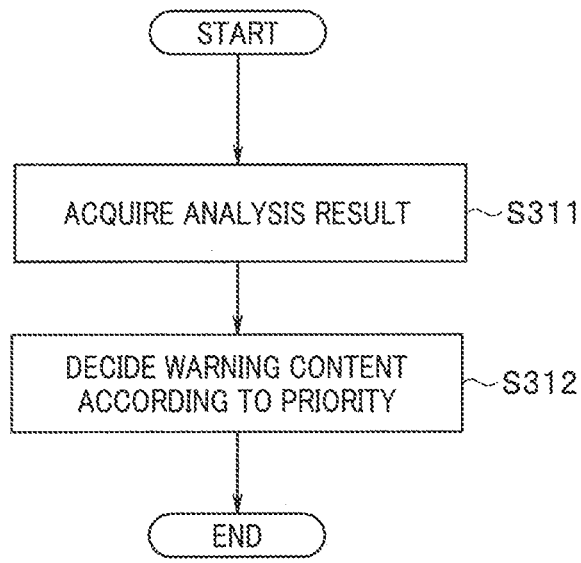
FIG. 8 is a flowchart for describing one example of the flow of warning content decision processing according to the second embodiment.

When the function propriety analysis processing shown in FIG. 7 is finished, S31 in FIG. 6 is then executed. The processing in S31 is executed by the procedure shown in FIG. 8, for example. FIG. 8 is a flowchart for describing one example of the flow of warning content decision processing according to the second embodiment. The warning content decision unit 352A shown in FIG. 3B relates to the processing shown in FIG. 8.

First, the analysis result acquired by the processing shown in FIG. 7 is acquired from the equipment state analysis unit 351A (S311). In the processing shown in FIG. 7, the analysis is executed on the plurality of items. In S311, the results of all items on which the analysis is executed are acquired from the equipment state analysis unit 351A.

Next, by referring to priority (the priority order as the warning content) given to the analysis items based on the magnitude of the influence contributing to the diagnosis support function, a factor affecting the execution of the diagnosis support function from the analysis result acquired in S311 is identified as the warning content. The priority is stored in advance in a memory or the like not shown in the drawing in the image processing device 32. In executing S311, the warning content is identified by reference to the memory.

The above-mentioned three items are, in descending order of an influence contributing to the diagnosis support function, (A) system equipment state, (B) image pickup state, and (C) operation state. For example, when the image pickup state of the generated image and the operation state made by the user are appropriate for the diagnosis support function, but the system equipment state is not appropriate for the diagnosis support function, the diagnosis support function does not act. Therefore, it can be said that (A) system equipment state has the largest influence contributing to the diagnosis support function. In the case where the system equipment state is appropriate for the diagnosis support function, even when the image pickup state of the generated image is not appropriate for the diagnosis support function, there is a possibility that the diagnosis support function can be activated with a reduced reliability of the support function. Further, in the case where the system equipment state is appropriate for the diagnosis support function, even when the operation state is not appropriate for the diagnosis support function, the diagnosis support function can be activated with reduced reliability of the support function. Accordingly, it can be said that (B) image pickup state has a smaller influence contributing to the diagnosis support function than (A) system equipment state, but has a larger influence contributing to the diagnosis support function than (C) operation state.

As described above, (A) system equipment state is set as the item having the highest priority. The item set to the second highest priority is (B) image pickup state, and (C) operation state is set as the item having the lowest priority.

In S311, from the analysis result acquired from the equipment state analysis unit 351A, the item which is determined to be not appropriate for the diagnosis support function is extracted. The analysis result relating to an item having the highest priority of the extracted items is decided as the warning content (S312).

When two items of (A) system equipment state and (B) image pickup state, for example, are selected as the analysis items, and the analysis result that the system equipment state is not appropriate for the diagnosis support function is acquired, it is decided that the analysis result of the system equipment state is the warning content regardless of the analysis result of the image pickup state. When two items of (B) image pickup state and (C) operation state are selected as the analysis items, and the analysis result that the image pickup state is not appropriate for the diagnosis support function is acquired, it is decided that the analysis result of the image pickup state is the warning content regardless of the analysis result of the operation state.

When two items of (A) system equipment state and (C) operation state are selected, and the analysis result that the system equipment state is not appropriate for the diagnosis support function is acquired, it is decided that the analysis result of the system equipment state is the warning content regardless of the analysis result of the operation state. Further, when three items of (A) system equipment state, (B) image pickup state, and (C) operation state are selected, and the analysis result that at least the system equipment state is not appropriate for the diagnosis support function is acquired, it is decided that the analysis result of the system equipment state is the warning content regardless of the analysis results of the image pickup state and the operation state. Further, when the analysis result that the system equipment state is appropriate for the diagnosis support function, but the image pickup state is not appropriate for the diagnosis support function is acquired, it is decided that the analysis result of the image pickup state is the warning content regardless of the analysis result of the operation state. A sequence of processing for deciding warning content shown in FIG. 8 is finished as described above.

According to the above-mentioned embodiment, the analysis is made, by using the generated image and/or the system information of the endoscope 21 and the video processor 31, on whether the execution of the diagnosis support function is affected with respect to the plurality of items. When there are items which are determined to have an influence, an item having a large influence contributing to the diagnosis support function is selected from the items, and it is decided that warning is the item having a large influence. Further, a method for solving the warning content is displayed on the display device 41 and hence, the user can always identify the action condition of the diagnosis support function, whereby the user can easily comprehend the main cause and the solution method when the endoscope 21 or the video processor 31 is in a state not appropriate for the action.

Third Embodiment

In the above-mentioned second embodiment, the analysis is made from the plurality of viewpoints by using the generated image and/or the system information of the endoscope 21 and the video processor 31. The present embodiment differs from the second embodiment in that an analysis is individually made on each viewpoint, and an analysis is made more specifically on whether the execution of the diagnosis support function is affected.

An image processing device of the present embodiment has a configuration substantially the same as the configuration of the image processing device 32 of the first embodiment. The same components are given the same reference symbols, and the repeated description will be omitted.

The action confirmation processing relating to the diagnosis support function and performed by the image processing device of the present embodiment is substantially the same as the processing procedures in the second embodiment shown in FIG. 4, FIG. 5, FIG. 6, and FIG. 7, but differs in that the procedure for analyzing the system equipment state (S21A), the procedure for analyzing the image pickup state (S21B), and the procedure for analyzing the operation state (S21C) in FIG. 7 are performed more specifically. Hereinafter, processing different from the processing in the second embodiment will be described.

Figure 9:
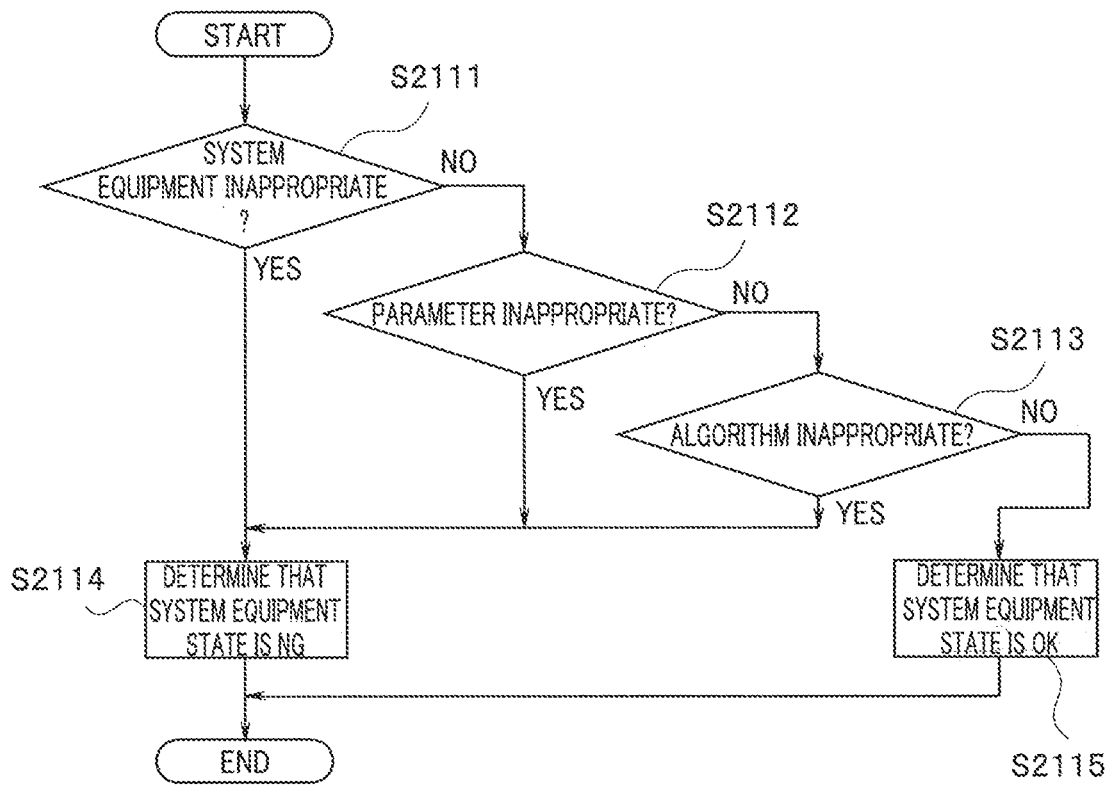
FIG. 9 is a flowchart showing one example of the flow of system equipment state analysis processing according to a third embodiment.

First, the procedure for analyzing the system equipment state (S21A) will be described. The processing in S21A is executed by the procedure shown in FIG. 9, for example. FIG. 9 is a flowchart showing one example of the flow of system equipment state analysis processing according to a third embodiment. The system equipment state analysis unit 351A1 shown in FIG. 3A relates to the processing shown in FIG. 9.

The system equipment state analysis unit 351A1, first, determines whether the system equipment per se forming the endoscope system, such as the endoscope 21 and the video processor 31, is in a state inappropriate for the diagnosis support function (S2111).

The detection of lesion and the generation of support information in the diagnosis support unit 34 are executed by using a support application in which different algorithms are set corresponding to the diagnosis target organ or a condition where the diagnosis support is performed (use purpose). An example of the diagnosis target organ may be the large intestine, the small intestine, the esophagus, or the stomach. Further, an example of the use purpose may be inspection or surgery. For example, a support application used for the diagnosis support in an inspection of the stomach differs from a support application used for an inspection of the large intestine. A support application used for the diagnosis support in an inspection of the esophagus differs from a support application used for the diagnosis support in surgery of the esophagus.

The endoscope 21 and the video processor 31 having a different specification and characteristics are used corresponding to the diagnosis target organ and the use purpose. For example, different kinds of endoscopes 21 are respectively used for an inspection of the upper digestive tract, such as the esophagus or the stomach, an inspection of the small intestine, an inspection of the large intestine, and laparoscopic surgery. Further, for example, different kinds of video processors 31 are respectively used for surgical inspections/procedures and internal medicine inspections/procedures.

Accordingly, when the kind of the endoscope 21 or the video processor 31 is not appropriate for the support application used by the diagnosis support unit 34, it is impossible to perform the diagnosis support by executing the support application. For example, when a support application for stomach inspection is selected in the diagnosis support unit 34, but the endoscope 21 for large intestine inspection or the surgical video processor 31, for example, is connected, the support application for stomach inspection cannot perform a normal action and hence, the diagnosis support function cannot be executed.

As described above, when the system equipment does not match the target organ for the algorithm of the support application set in the diagnosis support unit 34 or the use purpose, the system equipment state analysis unit 351A1 determines that the system equipment is in a state inappropriate for the diagnosis support function (S2111, YES).

Also in the case where the resolution of the image pickup unit 24 of the endoscope 21 is lower than the resolution necessary for the support application, the support application cannot perform the normal action and hence, the diagnosis support function cannot be executed. Accordingly, also when the resolution of the endoscope 21 is low, the system equipment state analysis unit 351A1 determines that the system equipment is in a state inappropriate for the diagnosis support function (S2111, YES).

Further, support applications are improved day by day, so upgraded support applications are provided and hence, the endoscope 21 and the video processor 31 which can be connected vary depending on the version. For example, when a support application which can process only digital data is set, and the video processor 31 for analog data is connected to the image processing device 32, data inputted from the video processor 31 cannot be processed by the support application and hence, the diagnosis support function cannot be executed.

As described above, also when the version or the function of the system equipment is a version or a function which cannot be handled by the support application set in the diagnosis support unit 34, the system equipment state analysis unit 351A1 determines that the system equipment is in a state inappropriate for the diagnosis support function (S2111, YES).

Note that the system information including the kind and version of the system equipment, such as the endoscope 21 and the video processor 31, and the resolution of the endoscope 21, for example, is acquired from memories or the like not shown in the drawing of the endoscope 21 and the video processor 31.

As described above, when it is determined that the system equipment is in a state inappropriate for the diagnosis support function (S2111, YES), the processing advances to S2114 where the system equipment state analysis unit 351A1 determines that the system equipment state is not appropriate for the diagnosis support function. Then, the system equipment state analysis unit 351A1 outputs the analysis result that the system equipment is inappropriate, and the system equipment state analysis processing is finished.

In contrast, when it is determined that the system equipment is in an appropriate state (S2111, NO), a parameter analysis unit 351A11 of the system equipment state analysis unit 351A1 determines whether the parameter of the system equipment forming the endoscope system, such as the endoscope 21 and the video processor 31, has a setting inappropriate for the diagnosis support function (S2112).

For example, assume the case where image highlighting, such as edge highlight processing or white balance correction processing, is performed in generating a generated image by the video processor 31. In such a case, when the highlight processing is performed in a state where the parameter of the highlight processing is set to a value exceeding a range predetermined for the diagnosis support function, the lesion part cannot be correctly detected and hence, the diagnosis support function cannot normally act.

As described above, also when the parameter of the system equipment forming the endoscope system is set to a value falling outside the range predetermined for the diagnosis support function, the parameter analysis unit 351A11 determines that the system equipment is in a state inappropriate for the diagnosis support function (S2112, YES). Then, the processing advances to S2114 where the system equipment state analysis unit 351A1 determines that the system equipment state is not appropriate for the diagnosis support function. Then, the system equipment state analysis unit 351A1 outputs the analysis result that the parameter of the system equipment is inappropriate, and the system equipment state analysis processing is finished.

In contrast, when it is determined that the parameter of the system equipment is also in an appropriate state (S2112, NO), the system equipment state analysis unit 351A1 determines whether the support application (the target organ for the algorithm, the use purpose, the version, and the like) set in the diagnosis support unit 34 is inappropriate (S2113).

When the target organ for the algorithm of the support application is not set, or a support application with an old version is set, the lesion part cannot be detected and hence, the diagnosis support function cannot normally act.

As described above, also when the support application set in the diagnosis support unit 34 is inappropriate, the system equipment state analysis unit 351A1 determines that the system equipment is in a state inappropriate for the diagnosis support function (S2113, YES). Then, the processing advances to S2114 where the system equipment state analysis unit 351A1 determines that the system equipment state is not appropriate for the diagnosis support function. Then, the system equipment state analysis unit 351A1 outputs the analysis result that the algorithm of the support application is inappropriate, and the system equipment state analysis processing is finished.

In contrast, when it is determined that the algorithm of the support application is also appropriate (S2113, NO), the system equipment state analysis unit 351A1 determines that the system equipment state is appropriate for the diagnosis support function (52115), and the system equipment state analysis processing is finished.

Figure 10:
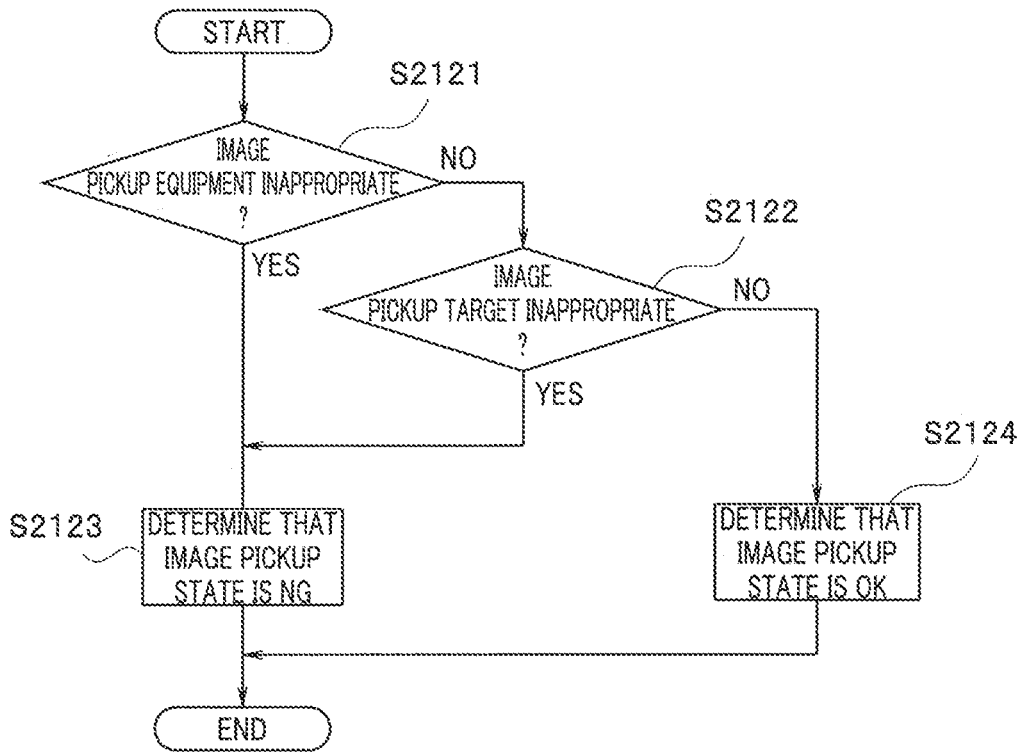
FIG. 10 is a flowchart showing one example of the flow of image pickup state analysis processing according to the third embodiment.

Next, the procedure for analyzing the image pickup state (S21B) will be described. The processing in S21B is executed by the procedure shown in FIG. 10, for example. FIG. 10 is a flowchart showing one example of the flow of the image pickup state analysis processing according to the third embodiment. The image pickup state analysis unit 351A2 shown in FIG. 3A relates to the processing shown in FIG. 10.

The image pickup state analysis unit 351A2, first, determines whether the state of the endoscope 21, which is image pickup equipment, is inappropriate for the diagnosis support function (S2121).

For example, when the image pickup target is not focused, when the exposure is inappropriate, or when a lens is fogged up, the generated image being the diagnosis support is not appropriately acquired and hence, the diagnosis support function does not normally act. In such a case, the image pickup state analysis unit 351A2 determines that the state of the image pickup equipment is inappropriate for the diagnosis support function (S2121, YES). Then, the processing advances to S2123 where the image pickup state analysis unit 351A2 determines that the image pickup state is not appropriate for the diagnosis support function. Then, the image pickup state analysis unit 351A2 outputs the analysis result that the state of the image pickup equipment is inappropriate, and the image pickup state analysis processing is finished.

In contrast, when it is determined that the state of the image pickup equipment is appropriate (S2121, NO), the image pickup state analysis unit 351A2 determines whether the generated image is inappropriate for the diagnosis support (S2122). When the generated image contains an image portion of debris, bleeding, or treatment scar, the lesion part cannot be detected or erroneously detected and hence, the diagnosis support function does not normally act. In such a case, the image pickup state analysis unit 351A2 determines that the image pickup target is in a state inappropriate for the diagnosis support function (S2122, YES). Then, the processing advances to S2123 where the image pickup state analysis unit 351A2 determines that the image pickup target is not in a state appropriate for the diagnosis support function. Then, the image pickup state analysis unit 351A2 outputs the analysis result that the state of the image pickup equipment is inappropriate, and the image pickup state analysis processing is finished.

In contrast, when it is determined that the image pickup target is also appropriate (S2122, NO), the image pickup state analysis unit 351A2 determines that the state of the image pickup equipment is appropriate for the diagnosis support function (52124), and the image pickup state analysis processing is finished.

Figure 11:
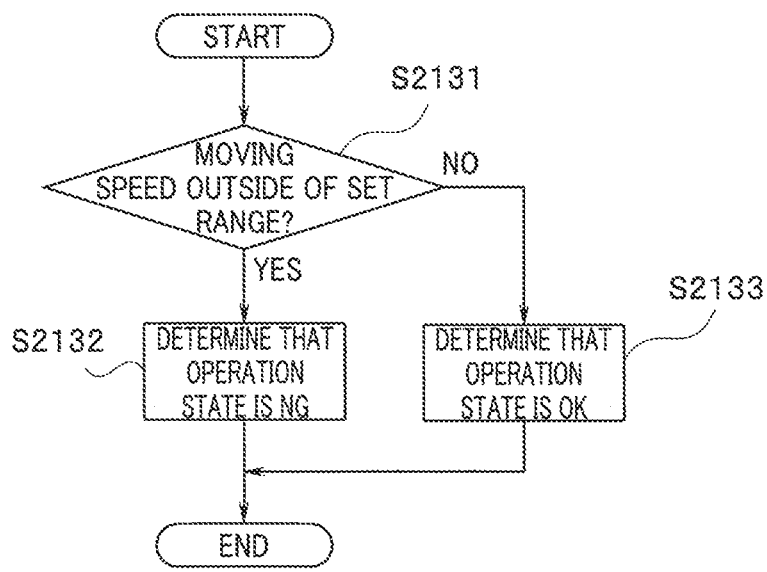
FIG. 11 is a flowchart showing one example of the flow of operation state analysis processing according to the third embodiment.

Lastly, the procedure for analyzing the operation state (S21C) will be described. The processing in S21C is executed by the procedure shown in FIG. 11, for example. FIG. 11 is a flowchart showing one example of the flow of operation state analysis processing according to the third embodiment. The operation state analysis unit 351A3 shown in FIG. 3A relates to the processing shown in FIG. 11.

The operation state analysis unit 351A3 determines whether the moving speed of the endoscope 21 falls outside the set range (S2131). Assume a case where observation is performed while withdrawing the distal end portion of the endoscope 21, such as an inspection of the large intestine or the upper digestive tract. In such a case, when the withdrawing speed is excessively high, it becomes difficult to detect the lesion part from the generated image, or a detection time period for detecting the lesion part is shortened and hence, the diagnosis support function does not normally act. In other words, when the diagnosis support function is executed, it is necessary to cause the endoscope 21 to move within a set speed range.

Accordingly, when the moving speed of the endoscope 21 falls outside the set range (S2131, YES), the operation state analysis unit 351A3 determines that the operation state is inappropriate for the diagnosis support function. Note that the withdrawing speed of the endoscope 21 is acquired by using a known technique for calculating speed, such as a technique for calculating speed from the difference between generated images of a plurality of frames, or a technique where a sensor which can detect speed, such as a gyro sensor, is provided at the distal end portion of the endoscope 21, and the value measured by the sensor is referred to, for example.

As described above, when it is determined that the operation state is inappropriate for the diagnosis support function (S2131, YES), the processing advances to S2132 where the operation state analysis unit 351A3 determines that the operation state is not appropriate for the diagnosis support function. Then, the operation state analysis unit 351A3 outputs the analysis result that the moving speed of the endoscope 21 falls outside the set speed range, and the operation state analysis processing is finished.

In contrast, when the moving speed of the endoscope 21 falls within the set speed range (S2131, NO), the operation state analysis unit 351A3 determines that the operation state is appropriate for the diagnosis support function (S2133), and the operation state analysis processing is finished.

As described above, with the finish of an analysis of whether the targeted analysis item is in a state where the targeted analysis item affects the diagnosis support function, a sequence of procedures of the display content generation processing (FIG. 6) based on the analysis result is executed.

As described above, according to the above-mentioned embodiment, the analysis is made in detail, by using the generated image and/or the system information of the endoscope 21 and the video processor 31, on whether the execution of the diagnosis support function is affected with respect to individual viewpoint. Therefore, when it is determined that the execution of the diagnosis support function is affected, a more specific cause can be identified and displayed on the display device 41 as warning. Accordingly, when the diagnosis support function is not acting, the user can rapidly respond to such a situation.

Fourth Embodiment

In the above-mentioned embodiment, when it is determined based on the analysis result from the acquired information analysis unit that the execution of the diagnosis support function is affected, the cause is identified, and the solution method for causing the diagnosis support function to appropriately act and the state of the diagnosis support function are displayed on the display device 41. The present embodiment differs in that these display contents are set more specifically.

Figure 12:
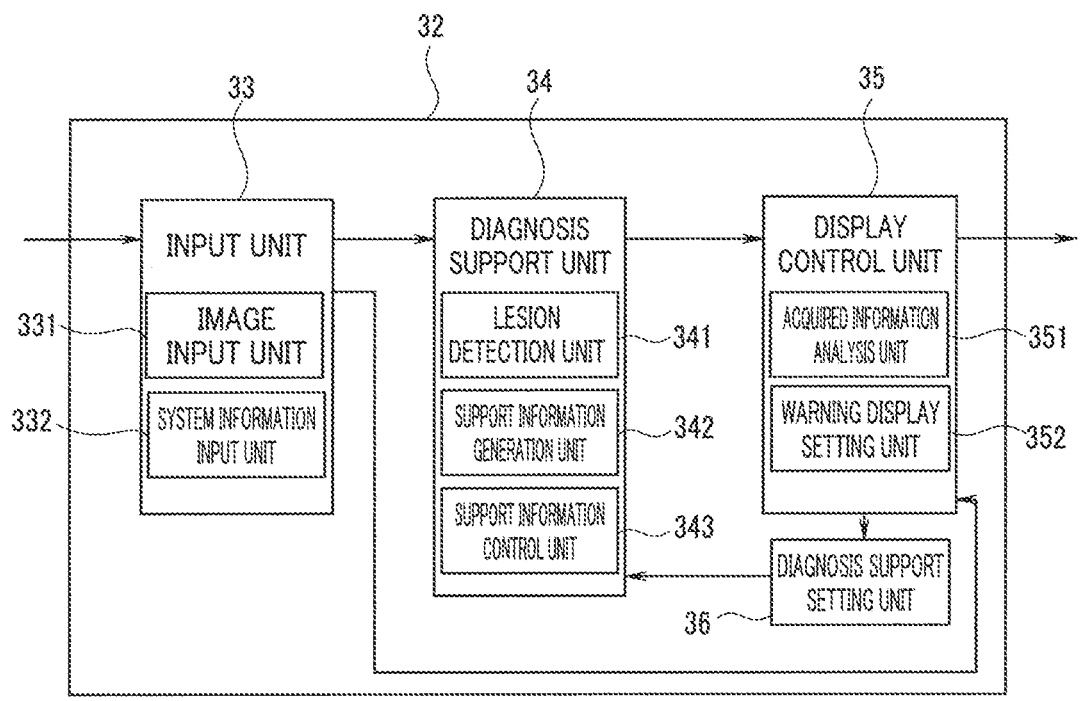
FIG. 12 is a block diagram for describing one example of a configuration relating to image processing performed by an image processing device according to a fourth embodiment.

FIG. 12 is a block diagram for describing one example of a configuration relating to image processing performed by an image processing device. The image processing device of the present embodiment has a configuration substantially the same as the configuration of the image processing device 32 of the first embodiment shown in FIG. 2 except for that a diagnosis support setting unit 36 is added. The same components are given the same reference symbols, and the repeated description will be omitted.

Based on the analysis result from the display control unit 35, the diagnosis support setting unit 36 controls whether the diagnosis support unit 34 executes the function. When the diagnosis support setting unit 36 performs control that the diagnosis support unit 34 does not execute the diagnosis support function (the diagnosis support unit 34 turns off the function per se), the generated images sequentially inputted from the image input unit 331 are directly outputted to the display control unit 35 without being processed by the diagnosis support unit 34.

Action confirmation processing relating to the diagnosis support function and performed by the image processing device of the present embodiment is substantially the same as the processing procedures shown in FIG. 4, FIG. 5, and FIG. 6, but differs in that the procedure shown in FIG. 6 for displaying the state of the diagnosis support function and the solution method (S32) is performed more specifically. Hereinafter, processing different from the processing in the first embodiment will be described.

Figure 13:
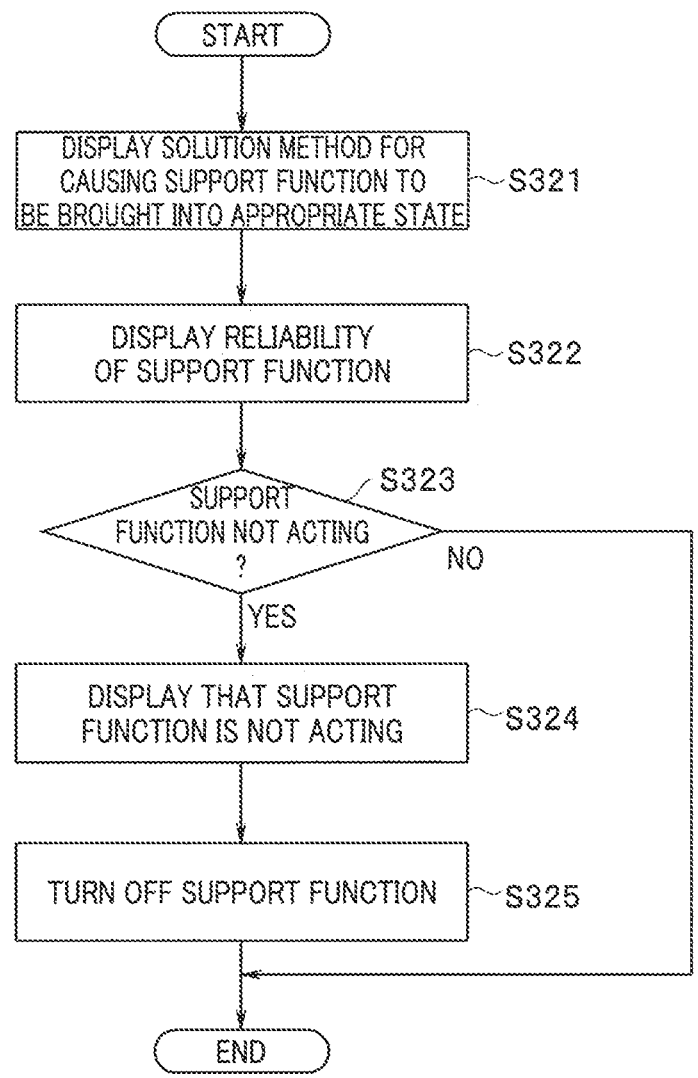
FIG. 13 is a flowchart showing one example of the flow of support function action information display processing according to the fourth embodiment.

The processing in S32 is executed by the procedure shown in FIG. 13, for example. FIG. 13 is a flowchart showing one example of the flow of support function action information display processing according to a fourth embodiment. Respective setting units (a solution method display setting unit 352B1, a reliability display setting unit 352B2, and a support impossibility display setting unit 352B3) included in the warning method setting unit 352B shown in FIG. 3B relate to the processing shown in FIG. 13.

First, the solution method display setting unit 352B1 derives a solution method for causing the diagnosis support function to act in an appropriate state, and outputs the solution method to the display device 41 (S321). In S321, the solution method display setting unit 352B1 causes a method for canceling warning to be displayed by reference to a factor affecting the execution of the diagnosis support function (warning content), which is identified in S31. For example, assume a case where warning that the system equipment state is not appropriate is decided, and the analysis result that the resolution of the endoscope 21 is excessively low is acquired in S31. In such a case, solution methods are derived such as "bring system equipment into appropriate state" based on the warning content, or "increase resolution of endoscope" based on the analysis result.

Next, the reliability display setting unit 352B2 decides reliability of the diagnosis support function, and outputs the reliability to the display device 41 (S322). Reliability is an index representing the degree of accuracy of output of the diagnosis support function (support content). For example, an index of 100 is assumed as a case where a lesion part is correctly detected, and appropriate support information is generated and displayed. An index of 0 is assumed as a case where any inappropriate state is generated, so a lesion part cannot be detected at all, or support information is not generated or displayed. The index is represented by a numerical value ranging from 0 to 100.

For example, when the system equipment is in an inappropriate state, the diagnosis support function cannot be executed and hence, reliability is 0. For example, when the image pickup target is in an inappropriate state due to the presence of debris in the generated image, the diagnosis support function acts, but accuracy in detection of the lesion part is reduced. In this case, an appropriate numerical value is calculated for reliability according to the condition of debris.

Next, the support impossibility display setting unit 352B3 determines whether the diagnosis support function is normally acting (S323). A determination whether the normal action is possible is made based on the analysis result from the equipment state analysis unit 351A. When the diagnosis support function cannot act (S323, YES), the support impossibility display setting unit 352B3 outputs, to the display device 41, the fact that the diagnosis support function is not acting (S324).

Then, the support impossibility display setting unit 352B3 outputs an instruction to stop the execution of the diagnosis support function to the support information control unit 343 of the diagnosis support unit 34 (S325). In other words, when the diagnosis support function does not normally act, and the cause of the abnormal action is not abnormality of the diagnosis support function per se, but is an external factor, such as a system equipment state, an image pickup state, or an operation state, the support impossibility display setting unit 352B3 prevents the diagnosis support function from continuing to act even when the correct support result cannot be acquired.

Note that the instruction to stop the execution of the diagnosis support function in S325 is not always required. When the support impossibility display setting unit 352B3 outputs the instruction to stop the execution of the diagnosis support function in S325, the support impossibility display setting unit 352B3 may output an instruction to restart the execution of the diagnosis support function to the support information control unit 343 of the diagnosis support unit 34 after the factor affecting the execution of the diagnosis support function is canceled, so the diagnosis support function is returned to a state where the diagnosis support function can normally act.

In contrast, when the diagnosis support function is not in a state where the diagnosis support function cannot act (S323, NO), a diagnosis support function action information display processing is finished.

Figure 14:
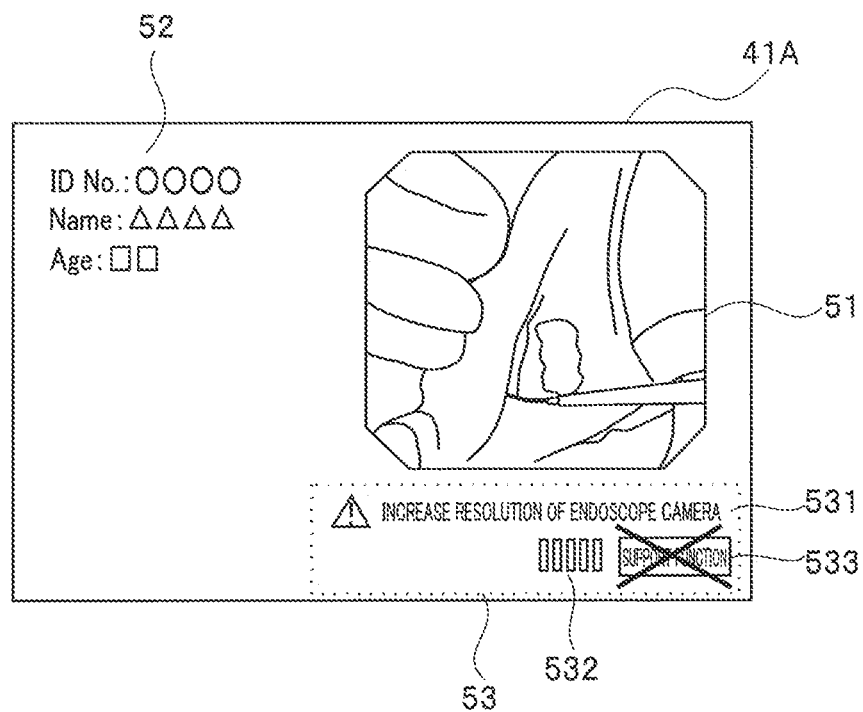
FIG. 14 is a view showing one example of a display image which is displayed on a display device via processing performed by the image processing device according to the fourth embodiment.

FIG. 14 is a view showing one example of the display image which is displayed on the display device via processing performed by the image processing device according to the fourth embodiment. A diagnosis support function state display unit 53 is disposed on the display screen 41A of the display device 41 together with a generated image display unit 51 and an inspection information display unit 52, for example. A solution method display unit 531, a reliability display unit 532, and a support function execution state display unit 533 are disposed on the diagnosis support function state display unit 53.

The solution method decided by the solution method display setting unit 352B1 is displayed on the solution method display unit 531 in a text format. Reliability decided by the reliability display setting unit 352B2 is displayed on the reliability display unit 532. In FIG. 14, the reliability display unit 532 displays reliability in the form of level meter. However, the reliability display unit 532 may display the reliability in other form, such as a numerical value. The support function execution state display unit 533 shows the action condition of the diagnosis support function per se. In FIG. 14, a cross mark is applied on an icon indicating the diagnosis support function to indicate that the action of the diagnosis support function is stopped. The support function execution state display unit 533 may also display the action condition of the diagnosis support function in other form in the same manner as the reliability display unit 532.

The display content and the arrangement of the diagnosis support function state display unit 53 shown in FIG. 14 are merely for the sake of example, and may be freely changed according to the preference of a user or visibility, for example.

As described above, according to the above-mentioned respective embodiments, the generated image and/or the system information are analyzed to determine and display whether the endoscope 21 or the video processor 31 is in a state where the endoscope 21 or the video processor 31 affects the action of the diagnosis support function and hence, the user can always identify the action condition of the diagnosis support function. Accordingly, when a highlighting display, such as a detection frame, is not performed, it can be easily identified whether the highlighting display is purposely not performed in order not to hinder the user's observation, or whether the diagnosis support function is not acting. Needless to say, the present invention is not limited to the above-mentioned embodiments, but various modifications and applications are conceivable without departing from the gist of the invention.

For example, the above description has been mainly made for the case where the present invention is the image processing device for an endoscope. However, the present invention is not limited to the image processing device for an endoscope. The present invention may be an image processing method for an endoscope, the image processing method performing processing substantially the same as the processing of the image processing device for an endoscope, a computer program which causes a computer to perform processing substantially the same as the processing of the image processing device for an endoscope, or a non-transitory recording medium which records the computer program, and is readable by a computer, for example.

What is claimed is:

1. An image processing device for an endoscope, comprising:
   a processor configured to:
      receive a generated image generated from an image of an object captured by an endoscope;
      calculate a withdrawing speed of the endoscope based on at least one of the generated image and sensor information relating to an operation state of the endoscope;
      detect a lesion part that is an observation target from the generated image;
      perform a diagnosis support action of adding support information to the generated image in which the lesion part was detected;
      determine whether the withdrawing speed of the endoscope is within a predetermined range; and
      in response to determining that the withdrawing speed of the endoscope is not within the predetermined range, determine that the lesion part cannot be detected or is erroneously detected, and control a display to display a warning content that the diagnosis support function is not performed normally.

2. The image processing device according to claim 1, wherein the processor is configured to:
   receive system information of system equipment including the endoscope;
   perform two or more of:
      a first determination of whether the lesion part cannot be detected or is erroneously detected based on the system information;
      a second determination of whether the lesion part cannot be detected or is erroneously detected based on an image pickup state of the generated image; and a third determination of whether the lesion part cannot be detected or is erroneously detected based on an operation state of the endoscope;
determine that one of a result of the first determination, a result of the second determination and a result of the third determination has a highest priority; and
in response to determining that the one of the result of the first determination, the result of the second determination and the one of the result of the third determination, determined to having the highest priority, is that the lesion part cannot be detected or is erroneously detected, control the display to display the warning content regardless of the other of the result of the first determination, the result of the second determination and the result of the third determination.

3. The image processing device according to claim 1, wherein the processor is configured to;
determine whether the lesion part cannot be detected or is erroneously detected based on an image pickup state of the generated image;
determine whether the lesion part cannot be detected or is erroneously detected based on an operation state of the endoscope; and
in response to determining that the lesion part cannot be detected or is erroneously detected based on the image pickup state, control the display to display the warning content regardless of a result of a determination of whether the lesion part cannot be detected or is erroneously detected based on the operation state of the endoscope.

4. The image processing device according to claim 1, wherein the processor is configured to;
receive system information of system equipment including the endoscope;
determine whether the lesion part cannot be detected or is erroneously detected based on the system information;
determine whether the lesion part cannot be detected or is erroneously detected based on an operation state of the endoscope; and
in response to determining that the lesion part cannot be detected or is erroneously detected based on the system information, control the display to display the warning content regardless of a result of a determination of whether the lesion part cannot be detected or is erroneously detected based on the operation state of the endoscope.

5. The image processing device according to claim 1, wherein the processor is configured to;
receive system information of system equipment including the endoscope;
determine whether the lesion part cannot be detected or is erroneously detected based on the system information;
determine whether the lesion part cannot be detected or is erroneously detected based on an image pickup state of the generated image; and
in response to determining that the lesion part cannot be detected or is erroneously detected based on the system information, control the display to display the warning content regardless of a result of a determination of whether the lesion part cannot be detected or is erroneously detected based on the image pickup state of the generated image.

6. The image processing device according to claim 1, wherein the processor is configured to;

receive system information of system equipment including the endoscope;
determine whether the lesion part cannot be detected or is erroneously detected based on the system information; and
in response to determining that the lesion part cannot be detected or is erroneously detected based on the system information, control the display to display the warning content.

7. The image processing device according to claim 1, wherein the processor is configured to;
receive a set parameter of system equipment including the endoscope;
determine whether the lesion part cannot be detected or is erroneously detected based on the set parameter of the system equipment; and
in response to determining that the lesion part cannot or is erroneously detected based on the set parameter, control the display to display the warning content.

8. The image processing device according to claim 7, wherein the set parameter of the system equipment comprises a value of a parameter of image highlight processing performed on the generated image or an image pickup signal from which the generated image is generated.

9. The image processing device according to claim 1, wherein the processor is configured to;
determine whether an algorithm which is set to execute the diagnosis support action is compatible with system equipment including the endoscope;
determine whether the lesion part cannot be detected or is erroneously detected based on a result of the determination of whether the algorithm which is set to execute the diagnosis support action is compatible with the system equipment including the endoscope; and
in response to determining that the lesion part cannot be detected or is erroneous detected based on the result of the determination of whether the algorithm which is set to execute the diagnosis support action is compatible with the system equipment including the endoscope, control the display to display the warning content.

10. The image processing device according to claim 1, wherein the processor is configured to;
determine, based on the generated image, whether the lesion part cannot be detected or is erroneously detected due to an image pickup state of the endoscope; and
in response to determining that the lesion part cannot be detected or is erroneously detected due to the image pickup state of the endoscope, control the display to display the warning content.

11. The image processing device according to claim 10, wherein the processor is configured to:
in determining whether the lesion part cannot be detected or is erroneously detected due to the image pickup state of the endoscope,
determine whether an image pickup target in the generated image is not focused; and
in response to determining that the image pickup target in the generated image is not focused, determine that the lesion part cannot be detected or is erroneously detected due to the image pickup state of the endoscope.

12. The image processing device according to claim 1, wherein the processor is configured to:

determine whether the lesion part cannot be detected or is erroneously detected due to a state of the object shown in the generated image; and in response to determining that the lesion part cannot be detected or is erroneously detected due to the state of the object shown in the generated image, control the display to display the warning content.

13. The image processing device according to claim 12, wherein the processor is configured to;

in determining whether the lesion part cannot be detected or is erroneously detected due to the state of the object shown in the generated image, determine whether an image portion including one or more of debris, bleeding and a treatment scar is present in the generated image; and in response to determining that the image portion including one or more of the debris, the bleeding and the treatment scar is present in the generated image, determine that the lesion part cannot be detected or is erroneously detected due to the state of the object shown in the generated image.

14. The image processing device according to claim 1, wherein the processor is configured to;

analyze at least one of the generated image and the information relating to the operation state of the endoscope to determine whether the lesion part cannot be detected or is erroneously detected due to one or more factors thereby causing the diagnosis support function to not perform normally, wherein the one or more factors includes the withdrawing speed of the endoscope being not within the predetermined range;

determine a solution method for removing the one or more factors; and control the display to display the solution method.

15. The image processing device according to claim 1, wherein the processor is configured to:

determine reliability of the diagnosis support action; and control the display to display the reliability of the diagnosis support action determined.

16. The image processing device according to claim 1, wherein the processor is configured to:

determine whether the lesion part cannot be detected or is erroneously detected due to one or more external factors thereby causing the diagnosis support function to not perform normally, wherein the one or more external factors includes determining that the withdrawing speed of the endoscope is not within the predetermined range; and in response to determining that the lesion part cannot be detected or is erroneously detected due to the one or more external factors, stop performing the diagnosis support action.

17. An image processing method for an endoscope, the image processing method comprising:

receiving a generated image generated from an image of an object captured by an endoscope;

calculating a withdrawing speed of the endoscope based on at least one of the generated image and sensor information relating to an operation state of the endoscope;

detecting a lesion part that is an observation target from the generated image;

performing a diagnosis support action of adding support information to the generated image in which the lesion part was detected;

determining the withdrawing speed of the endoscope is within a predetermined range; and in response to determining that the withdrawing speed of the endoscope is not within the predetermined range, determining that the lesion part cannot be detected or is erroneously detected and controlling a display to display a warning content that the diagnosis support function is not performed normally.

18. The image processing method according to claim 17, the image processing method further comprising:

receiving system information of system equipment including the endoscope;

performing two or more of:
a first determination of whether the lesion part cannot be detected or is erroneously detected based on the system information;
a second determination of whether the lesion part cannot be detected or is erroneously detected based on an image pickup state of the generated image;
a third determination of whether the lesion part cannot be detected or is erroneously detected based on an operation state of the endoscope;

determining that one of a result of the first determination, a result of the second determination and a result of the third determination has a highest priority; and in response to determining that the one of the result of the first determination, the result of the second determination and the one of the result of the third determination, determined to having the highest priority, is that the lesion part cannot be detected or is erroneously detected, control the display to display the warning content regardless of the other of the result of the first determination, the result of the second determination and the result of the third determination.

19. The image processing method according to claim 17, the image processing method further comprising:

receiving a set parameter of system equipment including the endoscope;

determining whether the lesion part cannot be detected or is erroneously detected based on the set parameter of the system equipment; and in response to determining that the lesion part cannot or is erroneously detected based on the set parameter, control the display to display the warning content.

20. The image processing method according to claim 17, the image processing method further comprising:

determining reliability of the diagnosis support action; and controlling the display to display the reliability of the diagnosis support action determined.

21. A non-transitory computer-readable recording medium storing a computer program that causes a computer to at least:

receive a generated image generated from an image of an object captured by an endoscope;

calculate a withdrawing speed of the endoscope based on at least one of the generated image and sensor information relating to an operation state of the endoscope;

detect a lesion part that is an observation target from the generated image;

perform a diagnosis support action of adding support information to the generated image in which the lesion part was detected; and determine whether the withdrawing speed of the endoscope is within a predetermined range; and in response to determining that the withdrawing speed of the endoscope is not within the predetermined range, determine that the lesion part cannot be detected or is erroneously detected, and control a display to display a warning content that the diagnosis support function is not performed normally.

22. The non-transitory computer-readable recording medium according to claim 21, wherein the computer program causes the computer to:
receive system information of system equipment including the endoscope;
perform two or more of:
a first determination of whether the lesion part cannot be detected or is erroneously detected based on the system information;
a second determination of whether the lesion part cannot be detected or is erroneously detected based on an image pickup state of the generated image; and
a third determination of whether the lesion part cannot be detected or is erroneously detected based on an operation state of the endoscope;
determine that one of a result of the first determination, a result of the second determination and a result of the third determination has a highest priority; and
in response to determining that the one of the result of the first determination, the result of the second determination and the one of the result of the third determination, determined to having the highest priority, is that the lesion part cannot be detected or is erroneously detected, control the display to display the warning content regardless of the other of the result of the first determination, the result of the second determination and the result of the third determination.

23. The non-transitory computer-readable recording medium according to claim 21, wherein the computer program causes the computer to:
receive a set parameter of system equipment including the endoscope;
determine whether the lesion part cannot be detected or is erroneously detected based on the set parameter of the system equipment; and
in response to determining that the lesion part cannot or is erroneously detected based on the set parameter, control the display to display the warning content.

24. The non-transitory computer-readable recording medium according to claim 21, wherein the computer program causes the computer to:
determine reliability of the diagnosis support action; and
control the display to display the reliability of the diagnosis support action determined.

* * * * *